US012089992B2

(12) United States Patent
Hagerstrom, III et al.

(10) Patent No.: US 12,089,992 B2
(45) Date of Patent: Sep. 17, 2024

(54) ULTRASOUND PROBE HOUSING WITH SINUSOIDAL INTERFACE AND ASSOCIATED DEVICES, SYSTEMS, AND METHODS

(71) Applicant: KONINKLIJKE PHILIPS N.V., Eindhoven (NL)

(72) Inventors: Victor Nils Hagerstrom, III, Reedsville, PA (US); James Christopher Taylor, State College, PA (US); Brett Corl, Reedsville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 168 days.

(21) Appl. No.: 17/786,018

(22) PCT Filed: Dec. 10, 2020

(86) PCT No.: PCT/EP2020/085423
§ 371 (c)(1),
(2) Date: Jun. 16, 2022

(87) PCT Pub. No.: WO2021/122264
PCT Pub. Date: Jun. 24, 2021

(65) Prior Publication Data
US 2023/0027155 A1 Jan. 26, 2023

Related U.S. Application Data

(60) Provisional application No. 62/949,051, filed on Dec. 17, 2019.

(51) Int. Cl.
*A61B 8/00* (2006.01)
*B29C 65/00* (2006.01)
(Continued)

(52) U.S. Cl.
CPC .......... *A61B 8/4444* (2013.01); *A61B 8/4483* (2013.01); *B29C 65/48* (2013.01); *B29C 65/58* (2013.01);
(Continued)

(58) Field of Classification Search
CPC ... A61B 8/4444; A61B 8/4455; B29C 66/221; B29C 66/54; B29C 66/1282; B29L 2031/3481
See application file for complete search history.

(56) References Cited

U.S. PATENT DOCUMENTS 5,740,947 A 4/1998 Flaig et al.
2004/0206850 A1 10/2004 Hafner
(Continued)

FOREIGN PATENT DOCUMENTS

CN 106089118 A 11/2016
DE 102014109295 B3 1/2016
(Continued)

OTHER PUBLICATIONS

International Search Report and Written Opinion for PCT/EP2020/085423, Mailing date: Apr. 13, 2021, 10 pages.

*Primary Examiner* — Colin T. Sakamoto
*Assistant Examiner* — Tommy T Ly

(57) ABSTRACT

The present application provides an ultrasound probe comprising a housing that includes a coupling interface having a sinusoidal geometry. The housing is formed by a first body (300) and a second body having opposite and corresponding sinusoidal geometries. The first body includes a first proximal portion (105) and a first distal portion (107). The first proximal portion comprises a first sinusoidal shape (326). The second body includes a second proximal portion and a second distal portion. The second proximal portion comprises an opposite second sinusoidal shape. The first body
(Continued)

and the second body are coupled to form a handle having a sinusoidal interface. Further, the first distal portion and the second distal portion form a head portion at which the ultrasound transducer assembly is disposed.

15 Claims, 15 Drawing Sheets

(51) Int. Cl.
  *B29C 65/48* (2006.01)
  *B29C 65/58* (2006.01)
  *B29L 31/00* (2006.01)
(52) U.S. Cl.
  CPC ...... *B29C 66/12841* (2013.01); *B29C 66/221* (2013.01); *B29C 66/54* (2013.01); *B29L 2031/753* (2013.01)

(56) References Cited

U.S. PATENT DOCUMENTS

| 2009/0061384 | A1 | 3/2009 | Thomssen et al. |
| 2019/0094349 | A1* | 3/2019 | Hasegawa ............ G01S 7/52084 |
| 2020/0196985 | A1* | 6/2020 | Mallory ............... A61B 8/4455 |

FOREIGN PATENT DOCUMENTS

| JP | 2016123536 A | 7/2016 | |
| KR | 101733732 B1 * | 5/2017 | ........... A61B 8/4444 |
| WO | 2016088037 A1 | 6/2016 | |

\* cited by examiner

ULTRASOUND PROBE HOUSING WITH SINUSOIDAL INTERFACE AND ASSOCIATED DEVICES, SYSTEMS, AND METHODS

CROSS-REFERENCE TO PRIOR APPLICATIONS

This application is the U.S. National Phase application under 35 U.S.C. § 371 of International Application No. PCT/EP2020/085423, filed on Dec. 10, 2020, which claims the benefit of U.S. Provisional Patent Application No. 62/949,051, filed on Dec. 17, 2019. These applications are hereby incorporated by reference herein.

TECHNICAL FIELD

The present disclosure relates generally to the structure of an ultrasound probe, and in particular, an ultrasound probe housing that includes a sinusoidal interface.

BACKGROUND

Ultrasound probes are used to non-invasively obtain ultrasound images, or sonograms, of the internal anatomical structures of patients. Ultrasound probes typically include a housing or body that forms a handle, and an ultrasound transducer assembly positioned at least partially inside the housing. Ultrasound probe housings have been developed with specific characteristics for use in medical environments. For example, it may be desired that ultrasound probes include housings that meet high cosmetic and ergonomic standards. It may also be desirable for these housings to be fully sterilizable, as they may be used with patients in a medical environment. Some conventional ultrasound probes that have been developed over the years to meet these standards present manufacturing challenges, such as high scrap rates due to cosmetic or ergonomic failures and high overall cost. In particular, reliability testing of ultrasound probe housings has revealed problems in joining portions of the housings together at bond lines (also referred to as seams, interfaces, or parting lines) that impacts the overall strength of the housings and being unable to resist impact, which has become a common source of housing failures.

Current ultrasound probe housings have not adequately addressed bond line failures. Further, current ultrasound probe housings are associated with other undesirable manufacturing processes and reliability complications. For example, bond line failures have been observed in housings using room temperature vulcanized silicone rubber (RTV) as a gap-filler, especially in ultramobile, sealed transducers. While the addition of epoxy-bonded ribs may help to improve bond line strength for ultrasound probe housings, it is only available at discrete locations of the housing, and it is associated with additional manufacturing process complexity and manufacturing time. Additionally, physical joining or fusing techniques may pose additional challenges, such as damage to sensitive electronics, regions of failure, and misalignment of the portions of the ultrasound probe housing. For example, some conventional housing designs include post-and-tube or crush-rib features for alignment and retention, which may be highly susceptible to shear load.

SUMMARY

The present application provides an improved interface for coupling portions of a medical device housing that includes a coupling interface having a sinusoidal geometry. The interface is formed between the two housing bodies, or halves, with opposite and corresponding sinusoidal geometries. By joining two housing bodies that include equal but opposite sinusoidal geometries, a near continuous interface is formed that is capable of effectively transferring shear loads. In this manner, the sinusoidal pattern creates a joining mechanism that facilitates component alignment while distributing balance under tensile, compressive and torsional loading. Further, the coupling interface may include snap-fit features for providing retention between both bodies of the housing. The incorporated sinusoidal snap-fit features remove the need for closing tools in production, and may decrease the assembly time.

According to one embodiment of the present disclosure, an ultrasound probe, comprises a housing comprising a first body and a second body, and an ultrasound transducer assembly. The first body includes a first proximal portion and a first distal portion, wherein the first proximal portion comprises a first sinusoidal shape. The second body includes a second proximal portion and a second distal portion. In one aspect, the second proximal portion comprises an opposite second sinusoidal shape. In another aspect, the first body and the second body are coupled such that the first sinusoidal shape engages with the second sinusoidal shape to form a sinusoidal interface. In another aspect, the first proximal portion and the second proximal portion form a handle configured to be grasped by a user. In another aspect, the first distal portion and the second distal portion form a head portion. The ultrasound transducer assembly is configured to obtain ultrasound data. In one aspect, the ultrasound transducer assembly is disposed at the head portion of the housing.

In some embodiments, the first body and the second body comprise a polymeric material. In some embodiments, the first body further comprises a first outer wall portion, wherein the second body comprises a second outer wall portion. In some embodiments, the first outer wall portion and the second outer wall portion extend alongside the first sinusoidal shape and the second sinusoidal shape, respectively. In some embodiments, the first outer wall portion and the second outer wall portion engage to form a straight interface when the first body is coupled to the second body. In some embodiments, the first outer wall portion and the second outer wall portion are shaped and arranged relative to the first sinusoidal shape and the second sinusoidal shape such that the first outer wall portion contacts the second outer wall portion when the first sinusoidal shape engages the second sinusoidal shape. In some embodiments, the first body comprises a protrusion disposed at the sinusoidal interface. In some embodiments, the second body comprises a groove disposed at the sinusoidal interface. In some embodiments, the protrusion and the groove lock when the first sinusoidal shape engages the second sinusoidal shape.

In some embodiments, the protrusion is positioned on an inner surface of the first outer wall portion, and wherein the groove is positioned on the first sinusoidal shape. In some embodiments, the first body comprises a plurality of protrusions disposed at the sinusoidal interface. In some embodiments, the second body comprises a plurality of grooves disposed at the sinusoidal interface such that the first body is configured to be coupled to the second body to form the housing by a tool-less assembly process. In some embodiments, the ultrasound probe further includes an adhesive applied between the first body and the second body at the sinusoidal interface. In some embodiments, the first sinusoidal shape comprises a plurality of projections and a plurality of recesses. In some embodiments, the first outer wall portion comprises a rim. In some embodiments, the plurality of projections is positioned above the rim. In some embodiments, the plurality of recesses is positioned at least partially below the rim.

In some embodiments, the ultrasound probe further includes a cable coupled to the housing, wherein the cable comprises a plurality of conductors electrically coupled to the ultrasound transducer assembly. In some embodiments, the housing comprises a first opening at a distal end of the housing and a second opening at a proximal end of the housing. In some embodiments, the ultrasound transducer assembly is positioned within the first opening, and wherein the cable is positioned within the second opening. In some embodiments, the sinusoidal interface extends between the first opening and the second opening. In some embodiments, the sinusoidal interface comprises a proximal segment extending along the handle, and a distal segment extending along the head portion, wherein the proximal segment and the distal segment comprise different sinusoidal geometries. In some embodiments, the first sinusoidal shape extends continuously along the first proximal portion and the first distal portion of the first body. In some embodiments, the second sinusoidal shape extends continuously along the second proximal portion and the second distal portion of the second body. In some embodiments, the sinusoidal interface comprises at least three periods. In some embodiments, the first sinusoidal shape is offset from the second sinusoidal shape by half a period.

According to another embodiment of the present disclosure, an ultrasound imaging system includes an ultrasound probe and a processor circuit in communication with the ultrasound probe. The ultrasound probe includes a housing and an ultrasound transducer assembly. The housing includes a first body and a second body. The first body includes a first proximal portion and a first distal portion, wherein the first proximal portion comprises a first sinusoidal shape. The second body includes a second proximal portion and a second distal portion. The second proximal portion comprises an opposite second sinusoidal shape. The first body and the second body are coupled such that the first sinusoidal shape engages with the second sinusoidal shape to form a sinusoidal interface. The first proximal portion and the second proximal portion form a handle configured to be grasped by a user. The first distal portion and the second distal portion form a head portion. The ultrasound transducer assembly is configured to obtain ultrasound data and is disposed at the head portion of the housing. The processor circuit is configured to generate an ultrasound image based on the ultrasound data and output the ultrasound image to a display in communication with the processor circuit.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
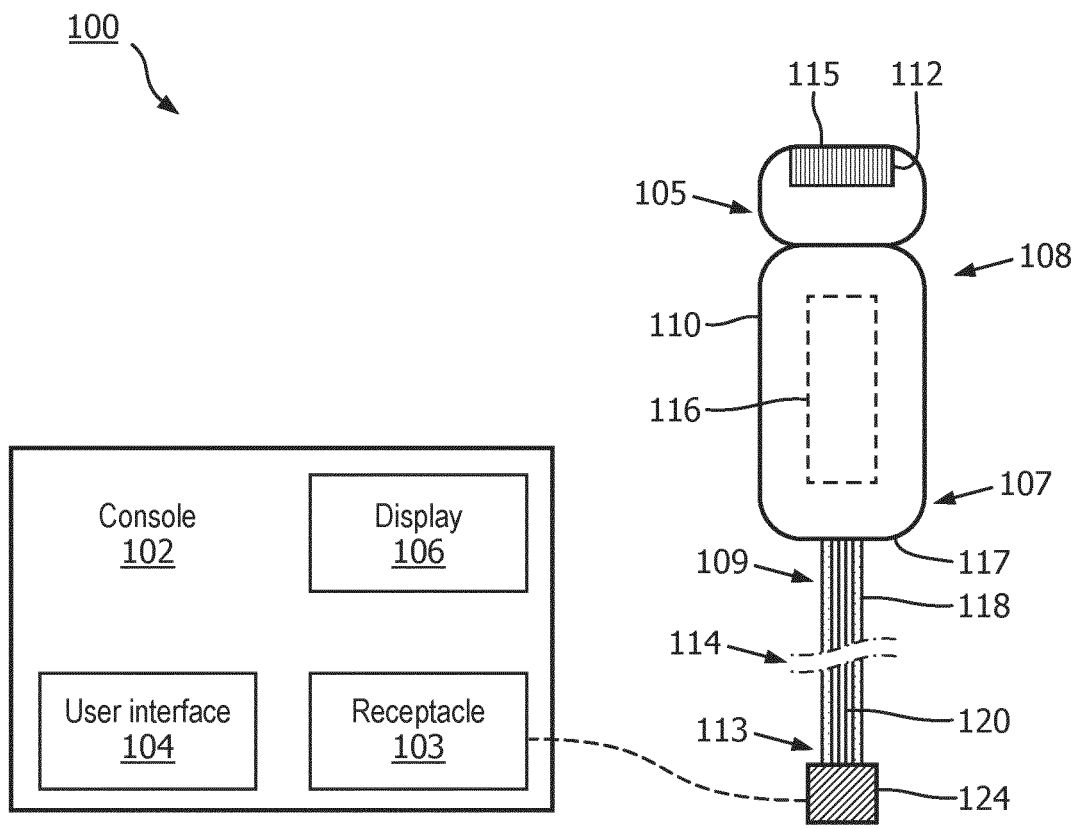
FIG. 1 is a diagrammatic schematic view of an ultrasound imaging system including a console and an ultrasound probe, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the medical device housings are discussed as ultrasound probe housings, it is understood that it is not intended to be limited to this application. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic view of an ultrasound imaging system 100, according to aspects of the present disclosure. The ultrasound imaging system 100 includes a console 102 and an ultrasound probe 108. The ultrasound imaging system 100 may be used to obtain and display ultrasound images of anatomy. In some circumstances, the system 100 may include additional elements and/or may be implemented without one or more of the elements illustrated in FIG. 1.

The ultrasound probe 108 is sized and shaped, structurally arranged, and/or otherwise configured to be placed on or near the anatomy of a subject to visualize anatomy inside of the subject's body. The subject may be a human patient or animal. The ultrasound probe 108 may be positioned outside the body of the subject. In some embodiments, the ultrasound probe 108 is positioned proximate to and/or in contact with the body of the subject. For example, the ultrasound probe 108 may be placed directly on the body of the subject and/or adjacent to the body of the subject. The view of the anatomy shown in the ultrasound image depends on the position and orientation of the ultrasound probe 108. To obtain ultrasound data of the anatomy, the ultrasound probe 108 can be suitably positioned and oriented by a user, such as a physician, sonographer, and/or other medical personnel, so that a transducer array 112 emits ultrasound waves and receives ultrasound echoes from the desired portion of the anatomy. The ultrasound probe 108 may be portable and suitable for use in a medical setting. In some instances, the ultrasound probe 108 can be referenced as an ultrasound imaging device, a diagnostic imaging device, external imaging device, transthoracic echocardiography (TTE) probe, and/or combinations thereof.

The ultrasound probe 108 includes a housing 110 structurally arranged, sized and shaped, and/or otherwise configured for handheld grasping by a user. The housing 110 can be referenced as a handle in some aspects. In other aspects, a proximal portion 107 of the housing 110 can be referenced as a handle. For example, the housing 110 may include a handle or handle portion and a probe head or head portion. The housing 110 surrounds and protects the various components of the imaging device 108, such as electronic circuitry 116 and the transducer array 112. Internal structures, such as a space frame for securing the various components, may be positioned within the housing 110. In some embodiments, the housing 110 includes two or more portions which are joined together during manufacturing. The housing 110 can be formed from any suitable material, including a plastic, a polymeric material, a composite, or combinations thereof.

The housing 110 and/or the ultrasound probe 108 includes the proximal portion 107 terminating at a proximal end 117 and a distal portion 105 terminating at a distal end 115. The proximal portion 107 may be referred to as a handle or handle portion, in some aspects, and may be graspable by a user. The distal portion 105 may be referred to as a probe head or head portion, and includes or houses an imaging assembly. All or a portion of the imaging assembly of the ultrasound probe 108 can define the distal end 115. The transducer array 112 can be directly or indirectly coupled to the housing 110. The operator of the ultrasound probe 108 may contact the distal end 115 of the ultrasound probe 108 to the body of the patient such that the anatomy is compressed in a resilient manner. For example, the imaging assembly, including the transducer array 112, may be placed directly on or adjacent to the body of the subject. In some instances, the distal portion 105 is placed directly in contact with the body of the subject such that the transducer array 112 is adjacent to the body of the subject.

The ultrasound probe 108 is configured to obtain ultrasound imaging data associated with any suitable anatomy of the patient. For example, the ultrasound probe 108 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood vessels, blood, chambers or other parts of the heart, and/or other systems of the body. The anatomy may be a blood vessel, such as an artery or a vein of a patient's vascular system, including cardiac vasculature, peripheral vasculature, neural vasculature, renal vasculature, and/or any other suitable lumen inside the body. In addition to natural structures, the ultrasound probe 108 may be used to examine man-made structures such as, but without limitation, heart valves, stents, shunts, filters and other devices.

The transducer array 112 is configured to emit ultrasound signals, and receive ultrasound echo signals corresponding to the emitted ultrasound signals. The echo signals are reflections of the ultrasound signals from anatomy with the subject's body. The ultrasound echo signals may be processed by the electronic circuitry 116 in the ultrasound probe 108 and/or in the console 102 to generate ultrasound images. The transducer array 112 is part of the imaging assembly of the ultrasound probe 108, including an acoustic window/lens and a matching material on a transmitting side of the transducer array 112, and an acoustic backing material on a backside of the transducer array 112. The acoustic window and the matching material have acoustic properties that facilitate propagation of ultrasound energy in desired directions (e.g., outwards, into the body of the patient) from the transmitting side of the transducer array 112. The backing material has acoustic properties that impede or limit propagation of ultrasound energy in undesired directions (e.g., inwards, away from the body of the patient) from the backside of the transducer array 112.

The transducer array 112 may include any number of transducer elements. For example, the array can include between 1 acoustic element and 10000 acoustic elements, including values such as 2 acoustic elements, 4 acoustic elements, 15 acoustic elements, 64 acoustic elements, 128 acoustic elements, 500 acoustic elements, 812 acoustic elements, 3000 acoustic elements, 9000 acoustic elements, and/or other values both larger and smaller. The transducer elements of the transducer array 112 may be arranged in any suitable configuration, such as a linear array, a planar array, a curved array, a curvilinear array, a circumferential array, an annular array, a phased array, a matrix array, a one-dimensional (1D) array, a 1.x dimensional array (e.g., a 1.5D array), or a two-dimensional (2D) array. The array of transducer elements (e.g., arranged in one or more rows, one or more columns, and/or one or more orientations) can be uniformly or independently controlled and activated. The transducer array 112 can be configured to obtain one-dimensional, two-dimensional, and/or three-dimensional images of patient anatomy. The ultrasound transducer elements may be piezoelectric/piezoresistive elements, piezoelectric micromachined ultrasound transducer (PMUT) elements, capacitive micromachined ultrasound transducer (CMUT) elements, and/or any other suitable type of ultrasound transducer elements.

The transducer array 112 is in communication with (e.g., electrically coupled to) the electronic circuitry 116. The electronic circuitry 116 can be any suitable passive or active electronic components, including integrated circuits (ICs), for controlling the transducer array 112 to obtain ultrasound imaging data and/or processing the obtained ultrasound imaging data. For example, the electronic circuitry 116 may include one or more transducer control logic dies. The electronic circuitry 116 may include one or more application specific integrated circuits (ASICs). In some embodiments, one or more of the ICs may comprise a microbeamformer (μBF), an acquisition controller, a transceiver, a power circuit, a multiplexer circuit (MUX), etc. In some embodiments, the electronic circuitry 116 may include a processor, a memory, a gyroscope, and/or an accelerometer. The electronic circuitry 116 is disposed within the ultrasound probe 108 and surrounded by the housing 110.

The ultrasound probe 108 includes a cable 114 to provide signal communication between the console 102 and one or more components of the ultrasound probe 108 (e.g., the transducer array 112 and/or the electronic circuitry 116). The cable 114 includes multiple electrical conductors 120 configured to carry electrical signals between the console 102 and the ultrasound probe 108. The electrical conductors 120 can be bare wires surrounded by one or more layers of insulating materials. The insulating materials are typically polymer-based composites, nylon, and/or polyvinyl chloride (PVC) synthetic plastic polymer. For example, electrical signals representative of the imaging data obtained by the transducer array 112 can be transmitted from the ultrasound probe 108 to the console 102 via the electrical conductors 120. Control signals and/or power can be transmitted from the console 102 to the ultrasound probe 108 via the electrical conductors 120. The cable 114 and/or electrical conductors 120 may provide any type of wired connection, such as a proprietary connection, an Ethernet connection, a Universal Serial Bus (USB) connection of any version or a mini USB of any version.

The cable 114 can also include a conduit 118 surrounding the electrical conductors 120. The conduit 118 is shaped as a tube and used to protect and route the electrical conductors 120 in the cable 114 of the ultrasound imaging device 108. The conduit 118 can be flexible and made of polymer, plastic, metal, fiber, other suitable materials, and/or combinations thereof. The conduit 118 protects the electrical conductors 120 by preventing their direct exposure to outside elements. A distal portion 109 of the cable 114 is coupled to the proximal portion 107 of the housing 110 of the ultrasound probe 108. The cable 114 may also include one or more strain relief structures positioned at the proximal portion 107 of the housing 110 and the connector 124.

A connector 124 is located at a proximal portion 113 of the cable 114. The connector 124 is configured for removably coupling with the console 102. Signal communication between the ultrasound probe 108 and the console 102 is established when the connector 124 is received within a receptacle 103 of the console 102. In that regard, the ultrasound probe 108 can be electrically and/or mechanically coupled to the console 102. The console 102 can be referenced as a computer or a computing device in some instances. The console 102 includes a user interface 104 and a display 106. The console 102 is configured to process the ultrasound imaging data obtained by the ultrasound probe 108 to generate an ultrasound image and output the ultrasound image on the display 106. A user can control various aspects of acquiring ultrasound imaging data by the ultrasound probe 108 and/or display of ultrasound images by providing inputs at the user interface 104. The imaging device 108 and the display 106 may be communicatively coupled directly or indirectly to the console 102.

One or more image processing steps can be completed by the console 102 and/or the ultrasound probe 108. The console 102 and/or the ultrasound probe 108 can include one or more processors in communication with memory. The processor may be an application-specific integrated circuit (ASIC), a field-programmable gate array (FPGA), a central processing unit (CPU), a digital signal processor (DSP), another hardware device, a firmware device, or any combination thereof configured to perform the operations described herein. In some embodiments, the memory is a random access memory (RAM). In other embodiments, the memory is a cache memory (e.g., a cache memory of the processor), magnetoresistive RANI (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In some embodiments, the memory may include a non-transitory computer-readable medium. The memory may store instructions. The instructions may include instructions that, when executed by a processor, cause the processor to perform operations described herein.

In some embodiments, the console 102 comprises a movable cart to which the user interface 104, the display 106, and processors are coupled. In some embodiments, the console 102 comprises a desktop computer. In some embodiments, the console 102 comprises a mobile device (e.g., a smart phone, a tablet, a laptop, or a personal digital assistant (PDA)) with integrated processor(s), memory, and display. For example, a touchscreen of the mobile device can be the user interface 104 and the display 106.

Figure 2:
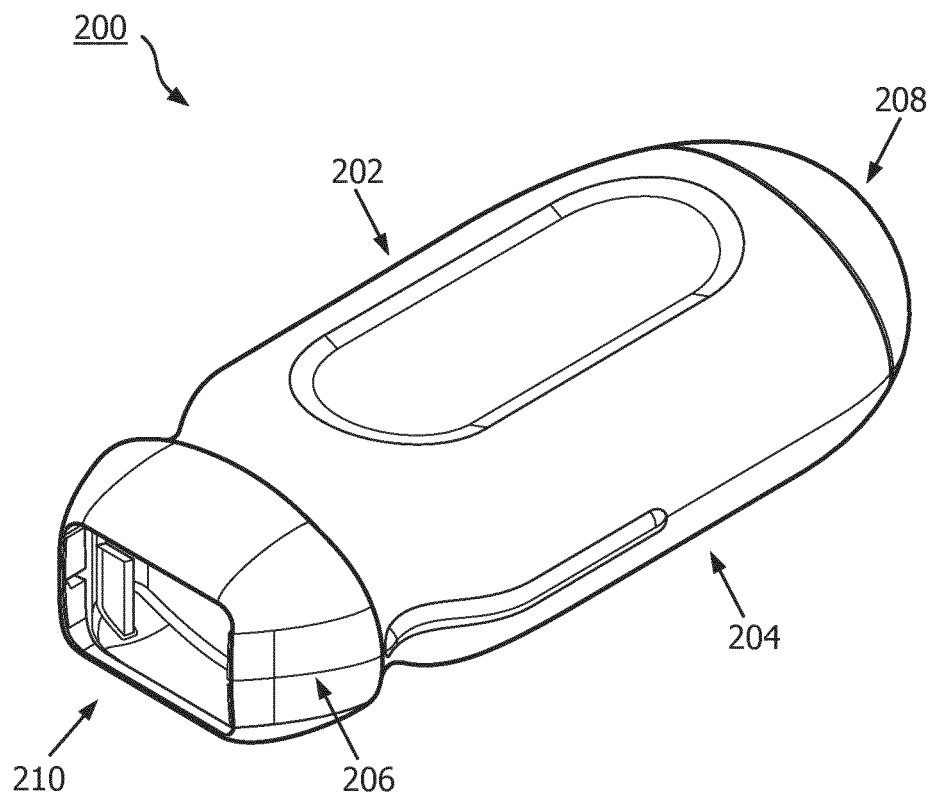
FIG. 2 is a perspective view of an ultrasound probe housing, according to embodiments of the present disclosure.

FIG. 2 shows an ultrasound probe housing 200 which includes a first body 202 and a second body 204 joined together along a seam, bond line, or interface 206. In that regard, the first and second bodies 202, 204 may be referred to as halves of the housing 200. The first body 202 and second body 204 are referred to in this way for ease of reference, however, the bodies 202, 204 may be distinguished in other ways, such as a male portion 202 and a female portion 204, upper and lower portions, etc. In some embodiments, the first body 202 and second body 204 are configured to be joined together with a tongue, groove type connection, and/or a sinusoidal snap-fit mechanism, which is described further below. In particular, the first body 202 may include an extension, extrusion, projection, or energy director and the second body 204 may include a groove, extrusion, projection, recess, or opening. However, the bodies 202, 204 may be joined in other ways, such as adhesive joining of substantially similar surfaces on both bodies 202, 204 or combination of adhesive and unique geometrical interface. Furthermore, although the housing 200 is shown as formed from two bodies 202, 204 that are relatively equal in size, it is understood that other numbers of bodies (i.e., three, four, or five portions) with various sizes may be used to form the housing 200. The bodies 202, 204 may be formed from a plastic or polymeric material. For example, the bodies 202, 204 may include acrylonitrile butadiene styrene (ABS), polysulfone (PSU), and polybutylene terephthalate (PBT). In some embodiments, the material can include glass fibers.

The housing 200 may be sized and shaped similarly to the handle 110 as discussed in FIG. 1. The housing 200 may include an opening 210 at a distal portion (i.e., for a transducer assembly) and an opening 208 at a proximal portion (i.e., for a data interface such as a connector or wires, such as the connector 124 and/or cable 114). The opening 208 at the proximal portion of the housing 200 may be configured to engage and/or couple to the conduit 118 and/or the strain relief feature of the cable 114. In an exemplary embodiment, the interface 206 extends longitudinally on both sides of the housing 200, along a length of the housing 200 from the proximal portion to the distal portion and/or from the opening 208 to the opening 210. The housing 200 may be sized and shaped to be grasped by a user and used in a medical environment. The first body 202 and second body 204 of the housing 200 may be joined together at the interface 206 by sinusoidal snap-fit mechanism, as discussed in more detail with reference to FIGS. 3-4. In some embodiments, a sealant is used, alone or in addition to the snap-fit mechanism. The sealant may including an epoxy applied over the sinusoidal interface 206, and cured to bond the first body 202 and the second body 204 at the interface 206. In some aspects, the housing 200 may be formed by introducing the sealant on one or both of the first body 202 and the female portion 204 and using the sinusoidal snap-fit mechanism to join the bodies 202, 204 through the sealant. The sinusoidal snap-fit mechanism may be positioned on and/or distributed between two housing halves (i.e. first body 202 and second body 204) with equal but opposite sinusoidal geometries in a form of a sine wave or periodic structure. When the first body 202 and the second body 204 are snapped or joined together they form a continuous interface joint that provides retention to both bodies 202, 204. The presence of the continuous interface 106 allows for more effective transferring of shear load along the length of the housing 200.

As mentioned above, in some embodiments, the bodies 202, 204 of the housing 200 couple or join to form an interface with a sinusoidal geometry. The interface 206 with sinusoidal geometry may increase the strength and/or resistance to impact of the transducer probe housing 200 by altering or distributing the load path throughout the housing. In that regard, the sinusoidal geometry may increase the contact area between the two housing bodies or halves, which ultimately facilitates load transfer. Stress balance may be achieved in the housing by offsetting tensile load with a corresponding compressive load. This may result in efficient load transfer at the housing interface 206 while reducing the presence of stress concentrations. In particular, the exemplary lateral interface 206 with sinusoidal geometry may prevent misalignment between the portions or bodies of the housing, which has been an issue in conventional probe housings.

Figure 3:
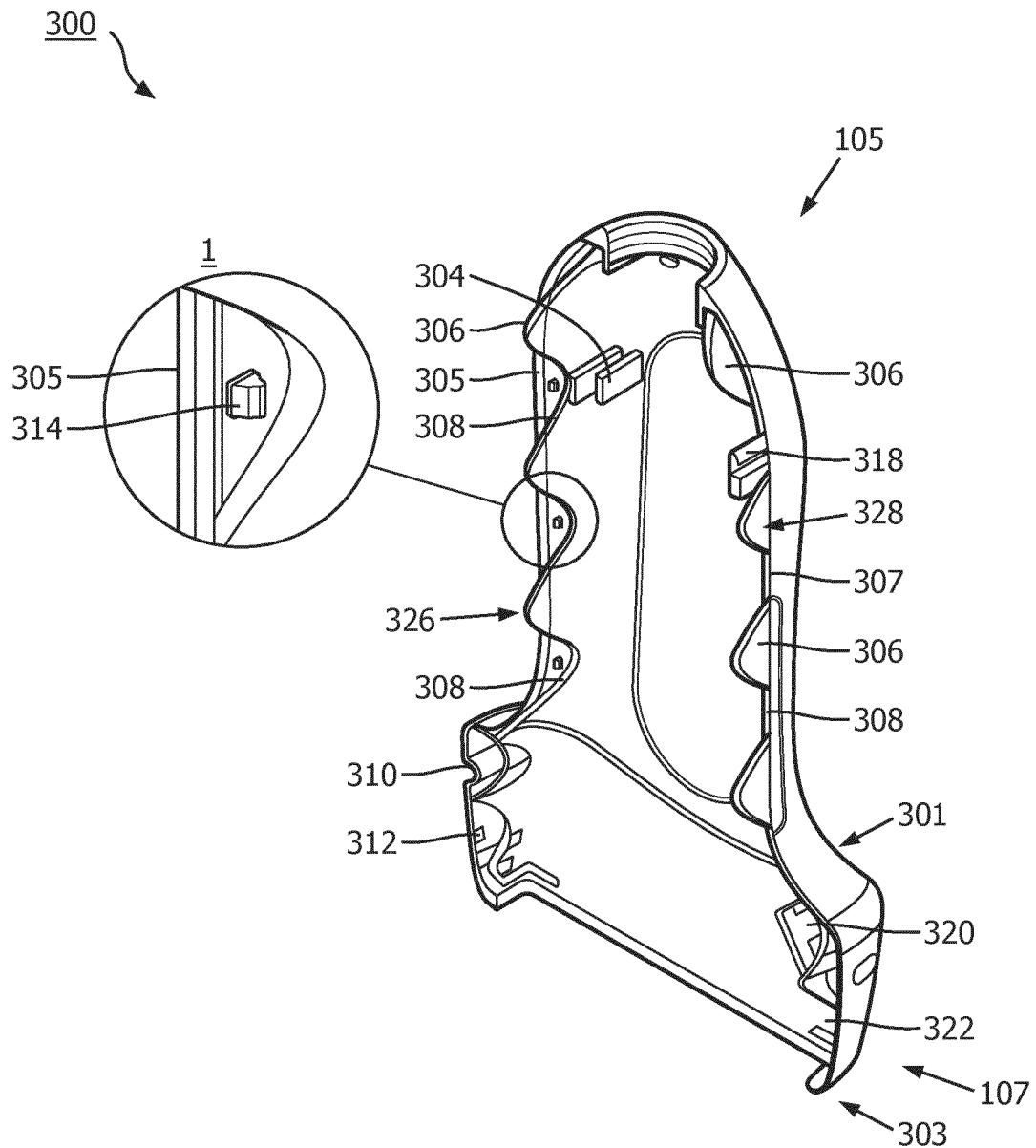
FIG. 3 is a perspective view of a first body of an ultrasound probe housing with sinusoidal interface geometry, according to embodiments of the present disclosure.

FIG. 3 is a perspective view of a first body 300 of an ultrasound probe housing with a sinusoidal interface, according to embodiments of the present disclosure. In some embodiments, the first body 300 includes a first proximal portion 105 and a first distal portion 107. The first body 300 includes a first sinusoidal shape or portion 326, a second sinusoidal shape 328, a first outer wall portion 305 extending alongside and positioned externally to the first sinusoidal shape 326, and a second outer wall portion 307 extending alongside and positioned externally to the second sinusoidal shape 328. The outer wall portions 305, 307 may also be referred to as edges, including a left edge and an opposite right edge, or a first edge and an opposite second edge. The outer wall portions 305, 307 are positioned on opposing sides of the first body 300 which may include geometries and/or features for joining the outer wall portions 305, 307 of the first body 300 with outer wall portions 405, 407 (FIG. 4) of the second body 300. The outer wall portions 305, 307 comprise flat or substantially flat rims that extend alongside the sinusoidal shapes 326, 328 from the distal portion 105 to the distal end 303 of the first body 300. The sinusoidal shapes 326, 328 form or comprise a first portion of a wall thickness of the first body 300, and the outer wall portions 305, 307 form or comprise a second portion of the wall thickness. In particular, the outer wall portions 305, 307 form an exterior portion of the wall thickness, and the sinusoidal shapes 326, 328 form an interior portion of the wall thickness. In other embodiments, the positions of the sinusoidal shapes 326, 328 and the outer wall portions 305, 307 may be switched such that the sinusoidal shapes 326, 328 comprise an exterior portion of the wall thickness and the outer wall portions 305, 307 comprise an interior portion of the wall thickness. It will be understood that the sinusoidal geometry may not be limited to sine wave types of curves and may comprise a variety of periodic geometries that include smooth curves, flat surfaces, pointed surfaces, and/or combinations thereof.

Figure 4:
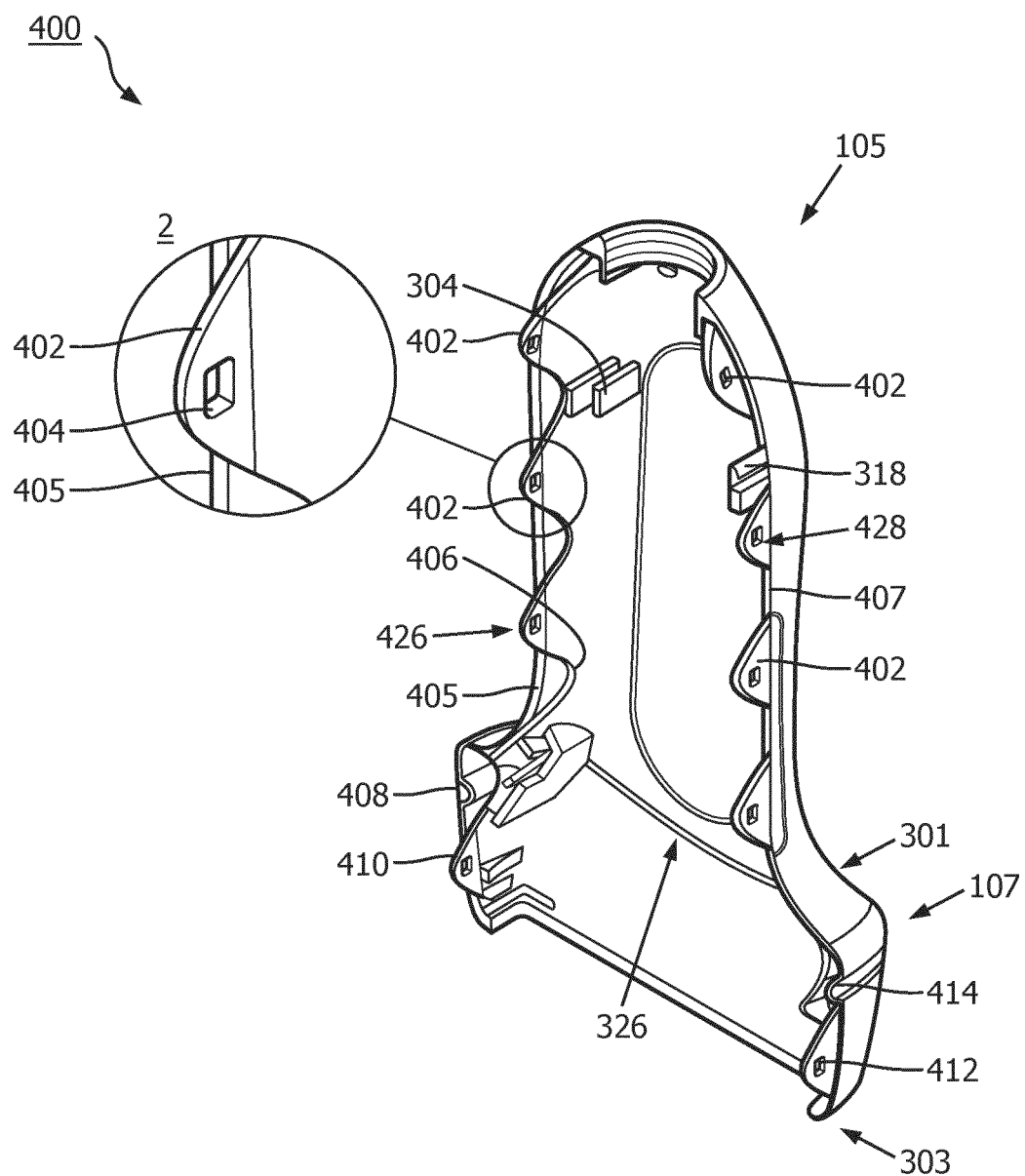
FIG. 4 is a perspective view of a second body of an ultrasound probe housing with sinusoidal interface geometry, according to embodiments of the present disclosure.

In the illustrated embodiment, the sinusoidal shapes 326, 328 include projections 306 and recesses 308 that extend from the tip of the proximal portion 105 to the proximal end 301 of the distal portion 107. The sinusoidal shapes 326, 328 may include features that are the same or different in size and/or amplitude from one another. In some embodiments, the projections 306 and the recesses 308 may be referred to as positive and negative amplitudes or concave and convex regions, however, different terminology may be used with respect to the geometry of these features. The distal portion 107 of the first body 300 includes additional recesses 310, 312 and projections 320, 322, which may form sinusoidal geometries different from the sinusoidal shapes 326, 328. In other embodiments, the sinusoidal shapes 326, 328 extend continuously from the proximal portion 105 to the distal portion 107. The features 310, 312, 320, 322 are positioned to join with or couple to the features 408, 410, 412, 414 of the second body 400 (FIG. 4). The features 310, 312, 320, 322 are positioned between proximal end 301 and the distal end 303 of the distal portion 107 of the first body 300. In some embodiments, the outer wall portions 305, 307 of the first body 202 may include features such as tongue-and-groove features, slots, protrusions, and/or other features for aligning and joining the bodies 300, 400. In particular, the first body 300 may include a retention feature 304 in a shape of hollow bar extending inward from an inner surface of the first body 300. The retention feature 304 is configured to fit within a protrusion 318 of the second body 204 (FIG. 4). In the illustrated embodiment, the first body 300 may include protrusion 318 positioned on an inner surface of the outer wall portion 307, and a flat rectangular shape configured to fit within the retention feature 304 of the second body 400 (FIG. 4). In the embodiment shown in FIG. 3, the recessed regions 306 of the first body 300 comprise locking protrusions 314 configured to be positioned within corresponding grooves or slots 404 (FIG. 4). The protrusions 314 may comprise barb-like features, and may be sized, shaped, and otherwise structurally arranged to be inserted into the grooves 404. In some aspects, the protrusions 314 and grooves 404 may be referred to as snap-fit features. The protrusions 314 and grooves 404 facilitate an attachment between the first body 300 and the second body 400. The protrusions 314 are formed to mate with the gaps 404 of the second body 400 (FIG. 4) when the first body 300 is aligned with and joined to the second body 400 and the sinusoidal shapes 326, 328 of the first body 300 engage the sinusoidal shapes 426, 428 of the second body 400. It will be understood that the locking features 314, 404 may include different structural geometries and/or retention components such as slot, dowel, interference fit, tongue-and-groove, latch, detent, and/or combinations thereof.

FIG. 4 is a perspective view of a second body 400 of an ultrasound probe housing with a sinusoidal interface, according to embodiments of the present disclosure. The second body 400 may include features similar or identical to those of the first body 300 shown in FIG. 3. In the illustrated embodiment, the second body 400 includes a second proximal portion 105 and a second distal portion 107. The second body 400 includes a first sinusoidal shape 426, a second sinusoidal shape 428, a first outer wall portion 405 extending alongside and positioned externally of the first sinusoidal shape 426, and a second outer wall portion 407 extending alongside and positioned externally of the second sinusoidal shape 428. The sinusoidal shapes 426, 428 include projections 402 and recesses 406. In the illustrated embodiment, the outer wall portions 405, 407, projections 402, and recesses 406 comprise shapes and dimensions that are complementary to the shapes and dimensions of the outer wall portions 305, 307, projections 306, and recesses 308 of the first body 300 of FIG. 3. In the embodiment of FIG. 4, the first and second sinusoidal shapes 426, 428 of the second body 400 are sized, shaped, and structurally arranged to engage with the first and second sinusoidal shapes 326, 328 of the first body 300 to form the sinusoidal interface. In that regard, the first and second sinusoidal shapes 426, 428 may include features, structures and sizes similar or complementary to those of the first and second sinusoidal shapes 326, 328 shown in FIG. 3. In particular, the projections 402 of the second body 400 include grooves 404 formed to mate with the protrusions 314 illustrated in FIG. 3. Further, the outer wall portions 405, 407 of the second body 400 are sized, shaped, and structurally arranged to form a straight interface when the sinusoidal shapes 326, 328 of the first body 300 engage the sinusoidal shapes 426, 428 of the second body, such that the outer wall portions 405, 407 of the second body 400 contact the outer wall portions 305, 307 of the first body 300. In the illustrated embodiment, the recesses 406 of the sinusoidal shapes 426, 428 of the second body 204 do not include any features such as grooves, protrusions, tongue etc. However, in other embodiments, the recesses 406 may comprise retention features, such as protrusions, grooves, slots, barbs, latches, or any other suitable feature to facilitate coupling of the first body 300 and second body 400.

It will be understood that, while the embodiments shown in FIGS. 2-4 describe probe housings formed of two bodies or halves, the present disclosure contemplates embodiments that include more than two bodies that include respective sinusoidal coupling interfaces, including three, four, five, or any other suitable number of bodies, both larger and smaller.

The sinusoidal interface formed between bodies of ultrasound probe housings can be tailored to different form factors and sizes by, for example, using different parameters of a sine wave equation in the form: $y=A \sin(Px)$, where parameters A and P represent the wave amplitude and period, respectively. The amplitude may be relatively similar between models with a nominal value of approximately 4 mm, and the period may be calculated based on the housing length and may have three or more periods per side. However, other amplitudes and/or periods are contemplated, including 1 mm, 2 mm, 3 mm, 5 mm, 10 mm, 15 mm, 30 mm, and any other value, both larger and smaller. The present disclosure also contemplates that the housing may include any suitable number of periods, including one, two, three, four, five, six, eight, ten, fifteen, twenty, or any other suitable number of periods, both larger and smaller. It will be also understood that the present disclosure contemplates that other probe housing types, shapes, and/or sizes other than those specifically illustrated.

The sinusoidal geometries and/or snap-fit features (e.g., protrusions 314, groove 404) of a probe housing may be constant between different probe housings of different sizes and types. The snap-fit features may be relatively small such that they can be used in smaller ultrasound probe housings or larger ultrasound probe housings. Use of the sinusoidal snap-fit interface in the production environment may simplify current production assembly processes. In some embodiments, a sealing adhesive is applied to the portions of the housing near the interface before the portions or bodies of the housing are snapped together. The adhesive may form a barrier layer that can reduce friction and wear between the bodies or portions of the housing. This may replace assembly process steps that include placing the housing in a closing fixture and/or torqueing screws to close the seam.

Figure 5:
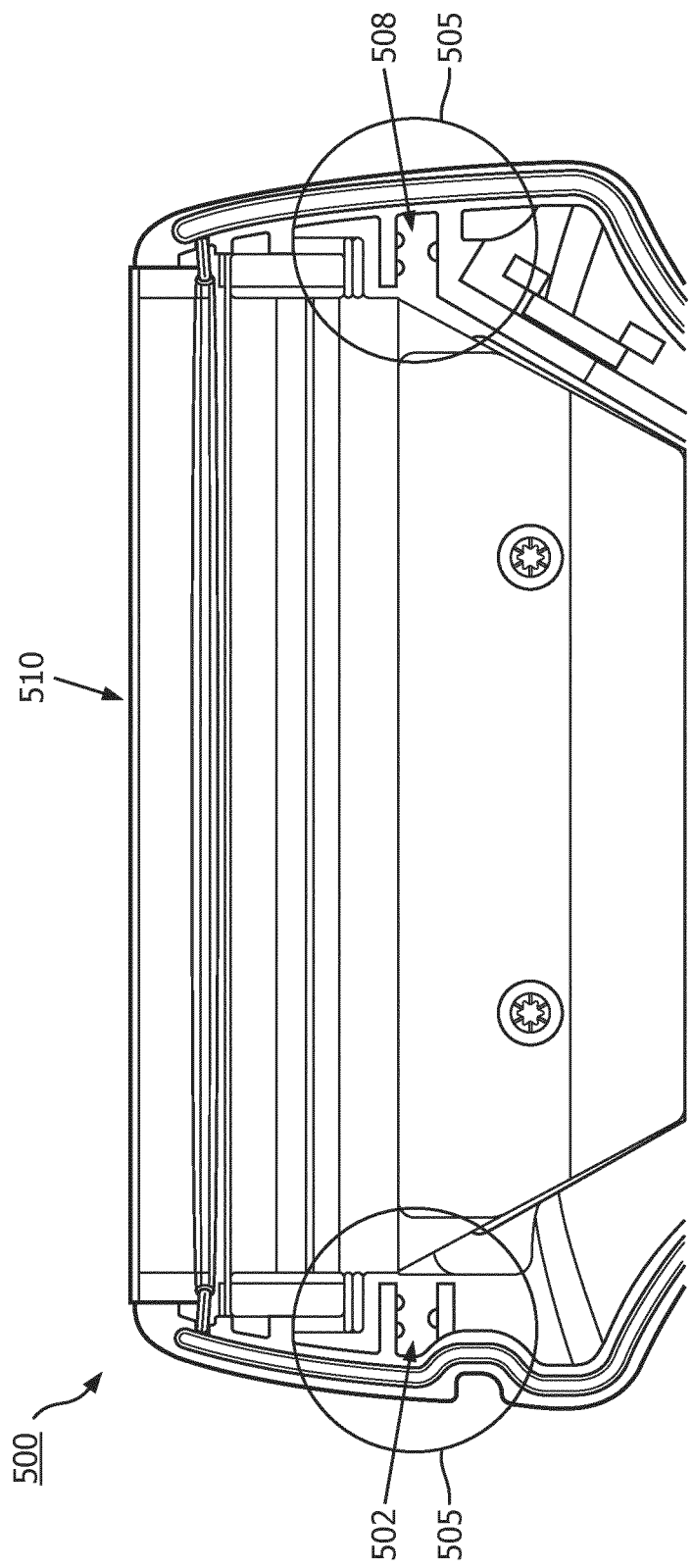
FIG. 5 is a cutaway view of an ultrasound probe housing that includes crush rib features, according to embodiments of the present disclosure.

FIG. 5 is a cutaway view of a head of a conventional ultrasound probe housing 500, which includes a standard crush rib architecture. An ultrasound transducer assembly 510 is coupled to the housing 500 and oriented to emit ultrasound energy distally of the probe housing 500. In the lateral regions 505, the conventional housing 500 lacks clearance on each edge 502, 508 between the outer wall of the probe housing 500 and the ultrasound transducer assembly 510. The lack of clearance in conventional housings can make the housings susceptible to damage of the components of the transducer assembly in the event of impact to the housing during handling and usage.

Figure 6:
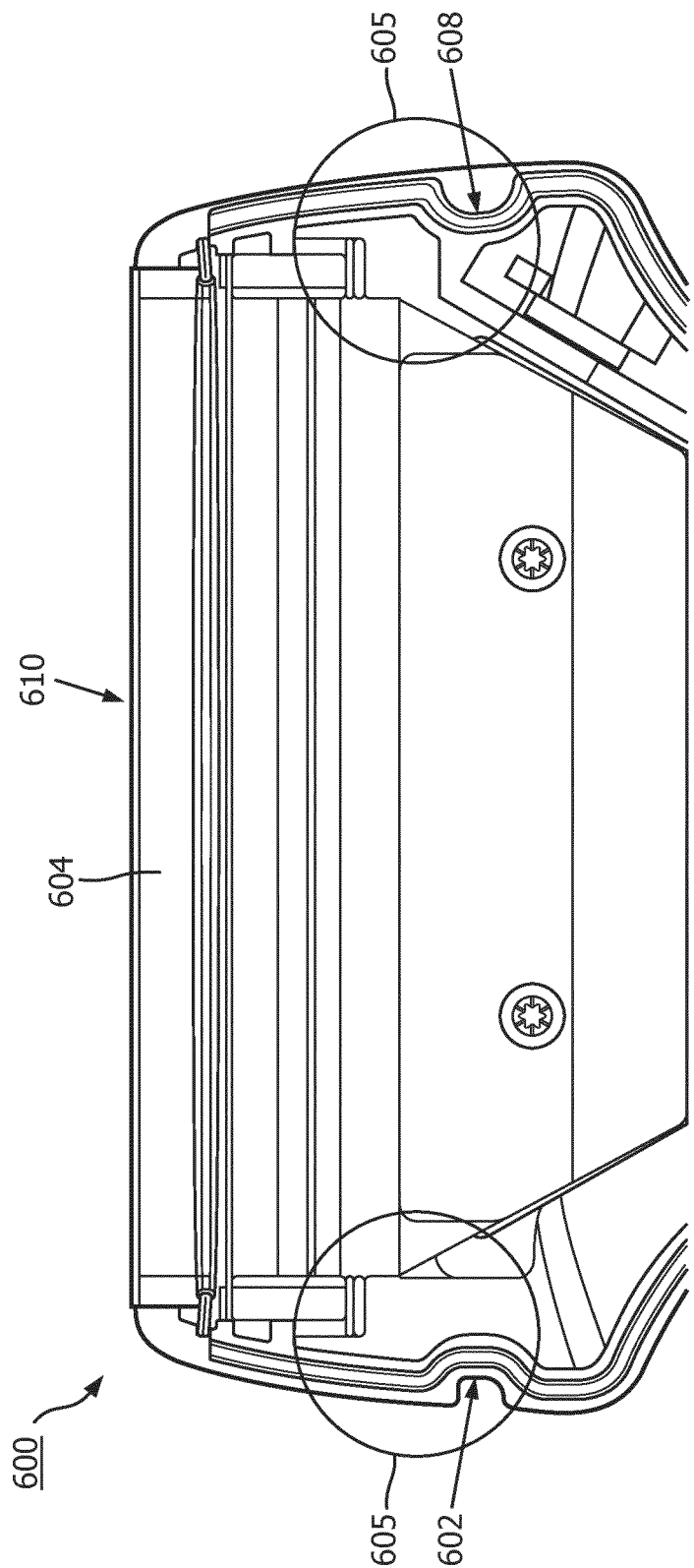
FIG. 6 is a cutaway view of an ultrasound probe housing that includes a sinusoidal snap-fit interface with clearance for electronic components, according to embodiments of the present disclosure.

FIG. 6 is a cutaway view of a head of an ultrasound probe housing 600 that includes a sinusoidal snap-fit interface, according to an embodiment of the present disclosure. The ultrasound probe housing 600 includes an ultrasound transducer assembly 610 positioned within and secured to the housing 600. In particular, the ultrasound transducer assembly 610 includes a transducer array 604 positioned at a distal end of the ultrasound transducer assembly and oriented to emit ultrasound energy distally of the housing 600. In the illustrated embodiment, the sinusoidal interface makes use of the wall thickness of the probe housing 600 and does not include crush rib features that protrude into the lateral regions 605 of the interior cavity of the housing 600. This allows more clearance on each edge 602, 608 between the walls of the housing 600 and the ultrasound transducer assembly 610, protecting the components of the transducer assembly 610 in the event of impact.

FIGS. 7-14 illustrate various physical and simulated failure analyses related to an ultrasound probe housing having a sinusoidal snap-fit interface, according to aspects of the present disclosure. The particular structure and/or materials of the probe can vary, but all embodiments may be sized and shaped, structurally arranged, and/or otherwise configured to exhibit properties such as: resistance to shock, uniform load transfer, improved alignment, elimination of design with sharp edges, and decrease mold complexity. For example, the probes associated with the analyses described below may comprise the shapes, features, and structural arrangements of the probes illustrated above with respect to FIGS. 2-4.

Figure 7A:
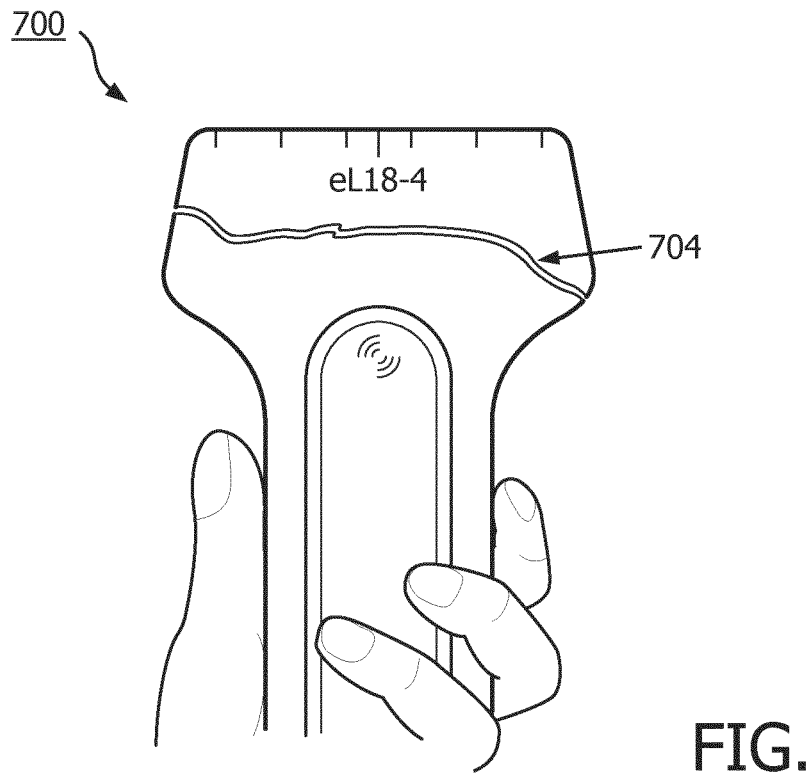
FIG. 7A is a perspective view of an ultrasound probe housing including crush ribs, according to embodiments of the present disclosure.
Figure 7B:
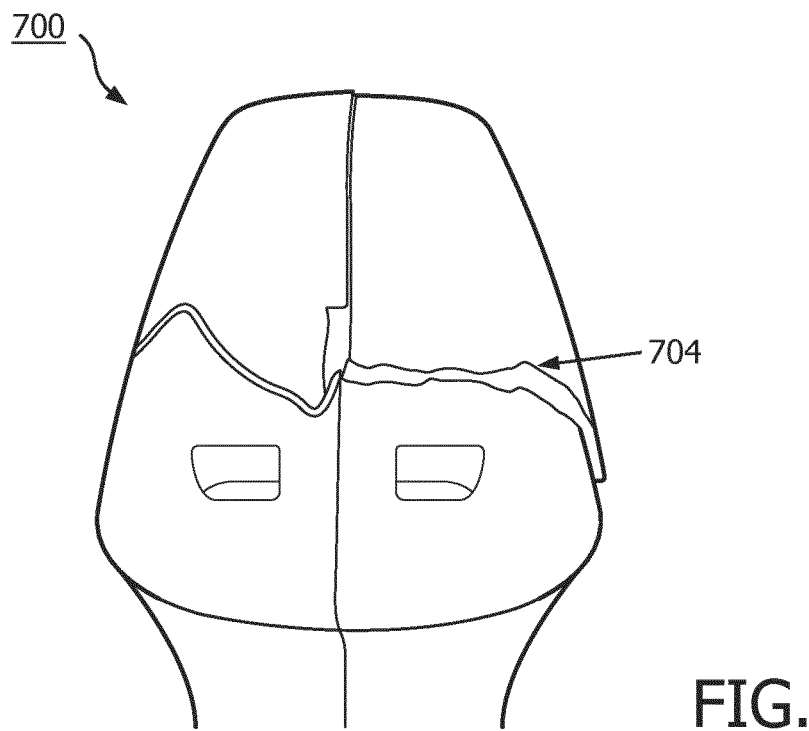
FIG. 7B is a perspective view of an ultrasound probe housing including crush ribs, design according to embodiments of the present disclosure.
Figure 8A:
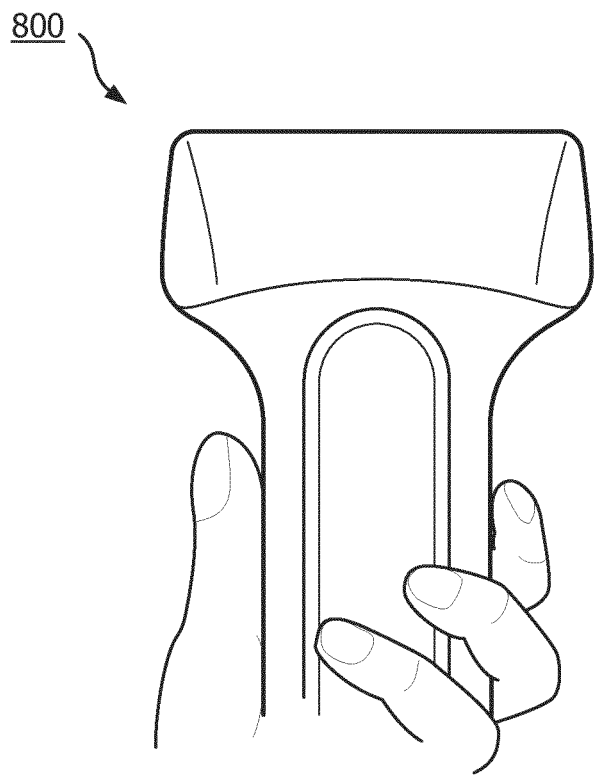
FIG. 8A is a perspective view of an ultrasound probe housing including a sinusoidal snap-fit interface, according to embodiments of the present disclosure.
Figure 8B:
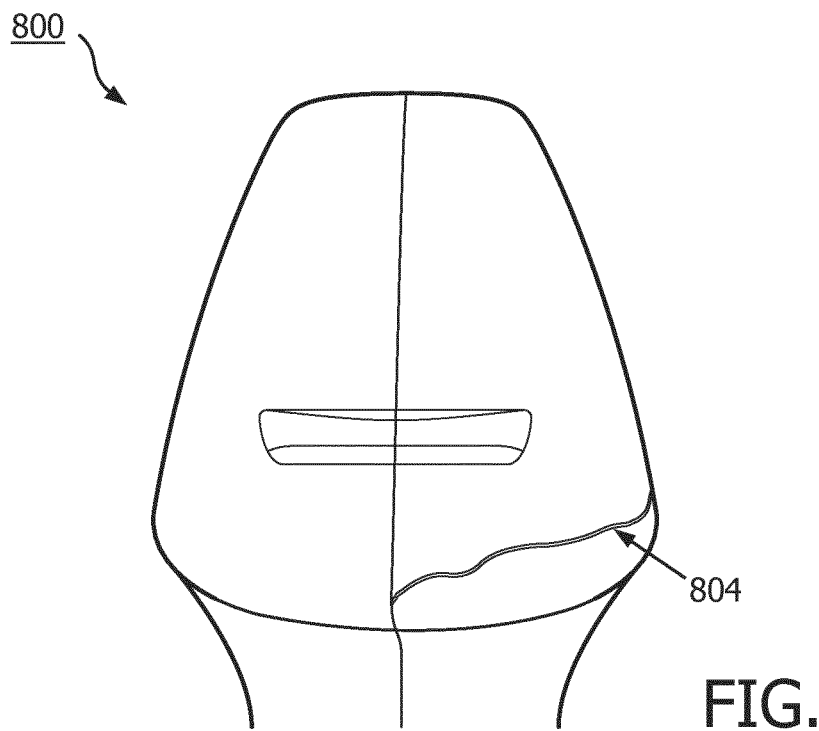
FIG. 8B is a perspective view of an ultrasound probe housing including a sinusoidal snap-fit interface, according to embodiments of the present disclosure.

FIGS. 7A and 7B are perspective views of a conventional probe housing 700 that includes a crush rib design. In particular, FIGS. 7A and 7B show the result of the conventional ultrasound probe housing 700 with crush ribs features, and fractures 704 caused by a drop test or impact test. The fracture 704 in the conventional probe is significant, and may be associated with the crush rib features. By contrast, FIGS. 8A and 8B are perspective views of probe housing 800 that includes a sinusoidal snap-fit construction 808 according to embodiments of the present disclosure. The probe housing 800 may be molded from the same material as the probe housing 700 of FIGS. 7A and 7B, and has undergone the same drop test as the transducer housing 700 illustrated in FIGS. 7A and 7B. As shown, the probe housing 800 with the sinusoidal interface exhibits an increased resistant to impact, as the fractures 804 were less severe.

Figure 9:
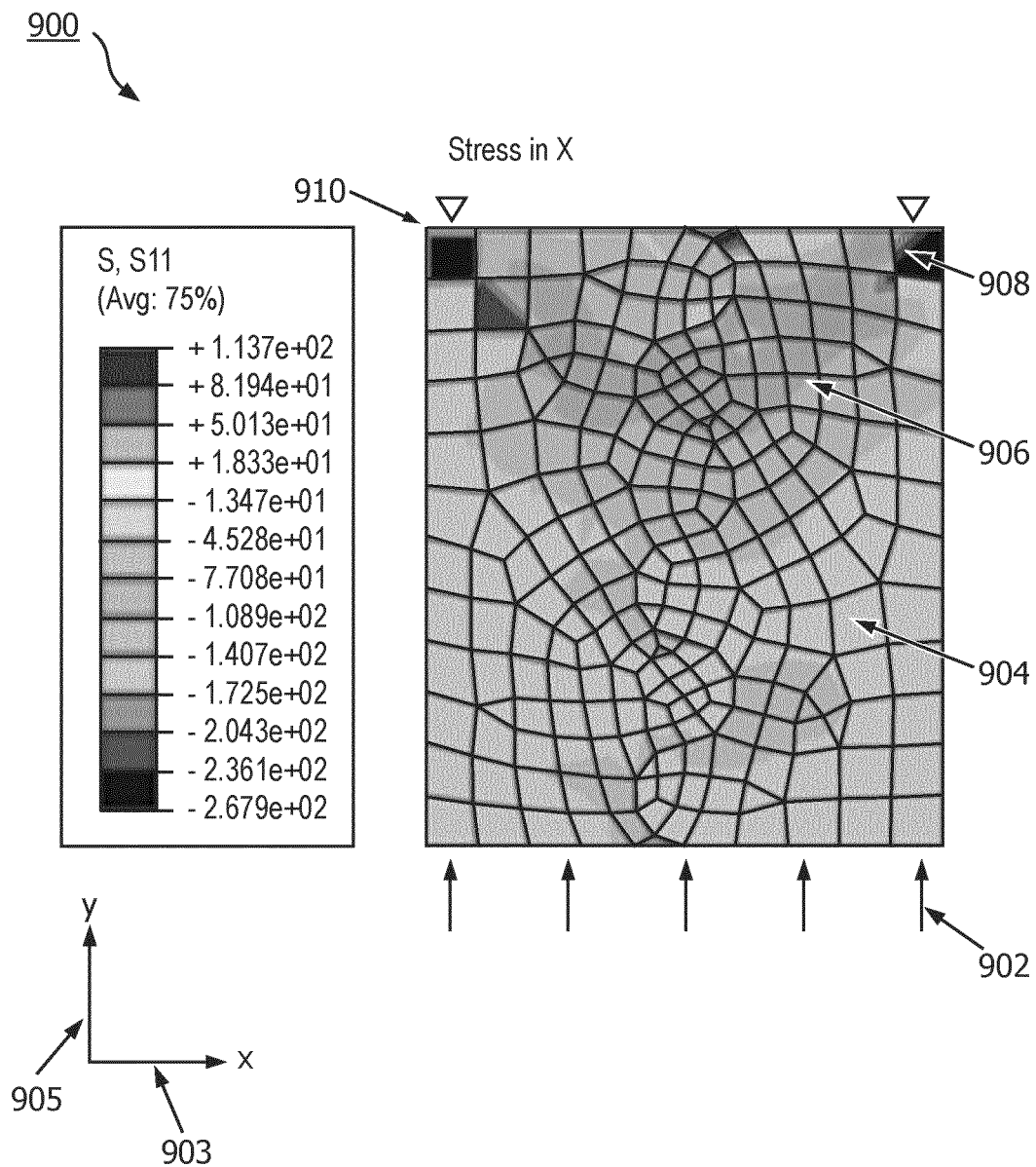
FIG. 9 is a graphical view of a finite element analysis model that demonstrates stress of an ultrasound probe housing in x-direction under axial loading conditions, according to embodiments of the present disclosure.

Further advantages of the exemplary sinusoidal snap-fit design interface between two bodies of an ultrasound probe housing is illustrated in FIGS. 9-14. In particular, FIGS. 9-14 illustrate results of simulated stress analyses under different loading conditions. In some embodiments, the simulated stress analysis may be performed using advanced finite element simulation software such as ANSYS, COMSOL, SolidWorks, Fluent, or combination thereof. To demonstrate the load transfer using the sinusoidal geometry, two simple finite element models were used one demonstrating an axial load (illustrated in FIGS. 9-11) and the other a shear load (illustrated in FIGS. 12-14). The results from the finite element analysis show that the sinusoidal interface effectively transferred load and reduced or eliminated areas of high stress concentrations on the sinusoidal interface. FIG. 9 shows a finite element analysis model 900 that demonstrates stress distribution points (e.g., 904, 906, 908, 910) in x-direction 903 under axial loading 902 conditions of an ultrasound probe housing with a sinusoidal interface according to embodiments of the present disclosure.

Figure 10:
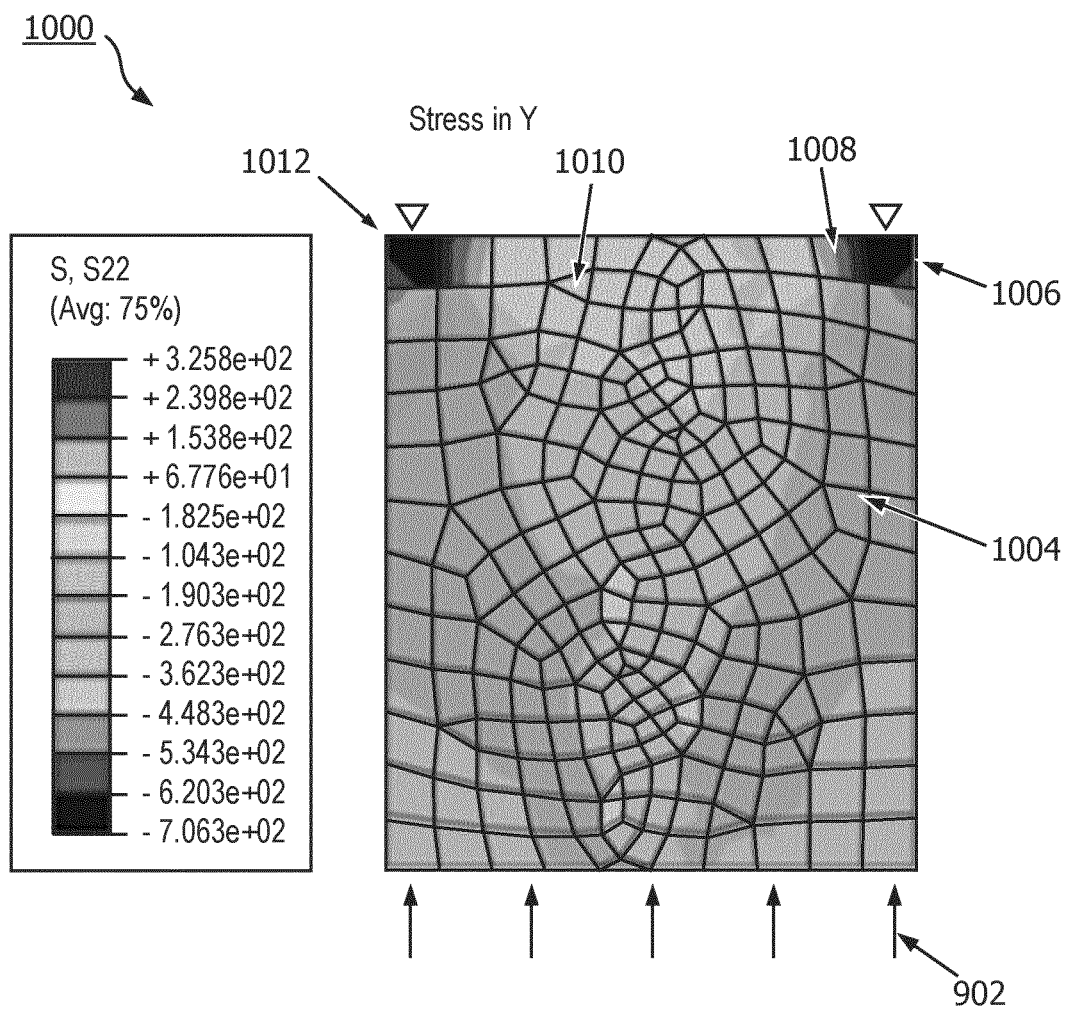
FIG. 10 is a graphical view of a finite element analysis model that demonstrates stress of an ultrasound probe housing in y-direction under axial loading conditions, according to embodiments of the present disclosure.
Figure 11:
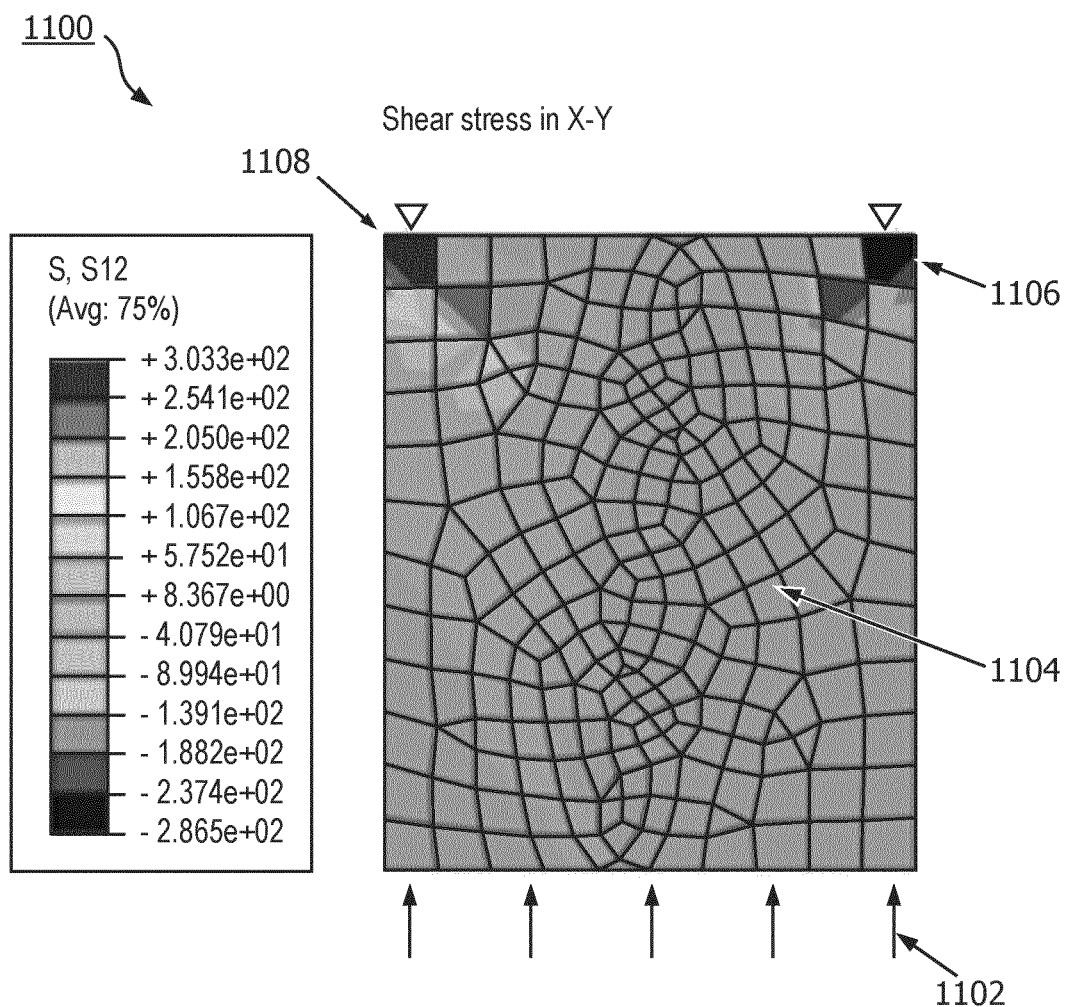
FIG. 11 is a graphical view of a finite element analysis model that demonstrates shear stress of an ultrasound probe housing in x-y-direction under axial loading conditions, according to embodiments of the present disclosure.

FIG. 10 illustrates finite element analysis model 1000 that demonstrates stress at distribution points (e.g., 1004, 1006, 1008, 1010, 1012), similar to model 900 as illustrated in FIG. 9, in y-direction 905 under axial loading 902 conditions of an ultrasound probe housing with a sinusoidal interface according to embodiments of the present disclosure. FIG. 11 illustrates a finite element analysis model 1100 that demonstrates shear stress distribution points (e.g., 1104, 1106, 1108) in x-y directions 903, 905 also under axial loading 1102 conditions of an ultrasound probe housing with a sinusoidal interface according to embodiments of the present disclosure. In the illustrated embodiments of FIGS. 9-11, the exemplary design with the sinusoidal interface under axial loading conditions resulted in effectively offsetting tensile and compressive stresses to be generated in the normal stress directions along x-axis (FIG. 9) and y-axis (FIG. 10) while the shear stress in the x-y direction (FIG. 11) was uniformly transferred across the interface.

Figure 12:
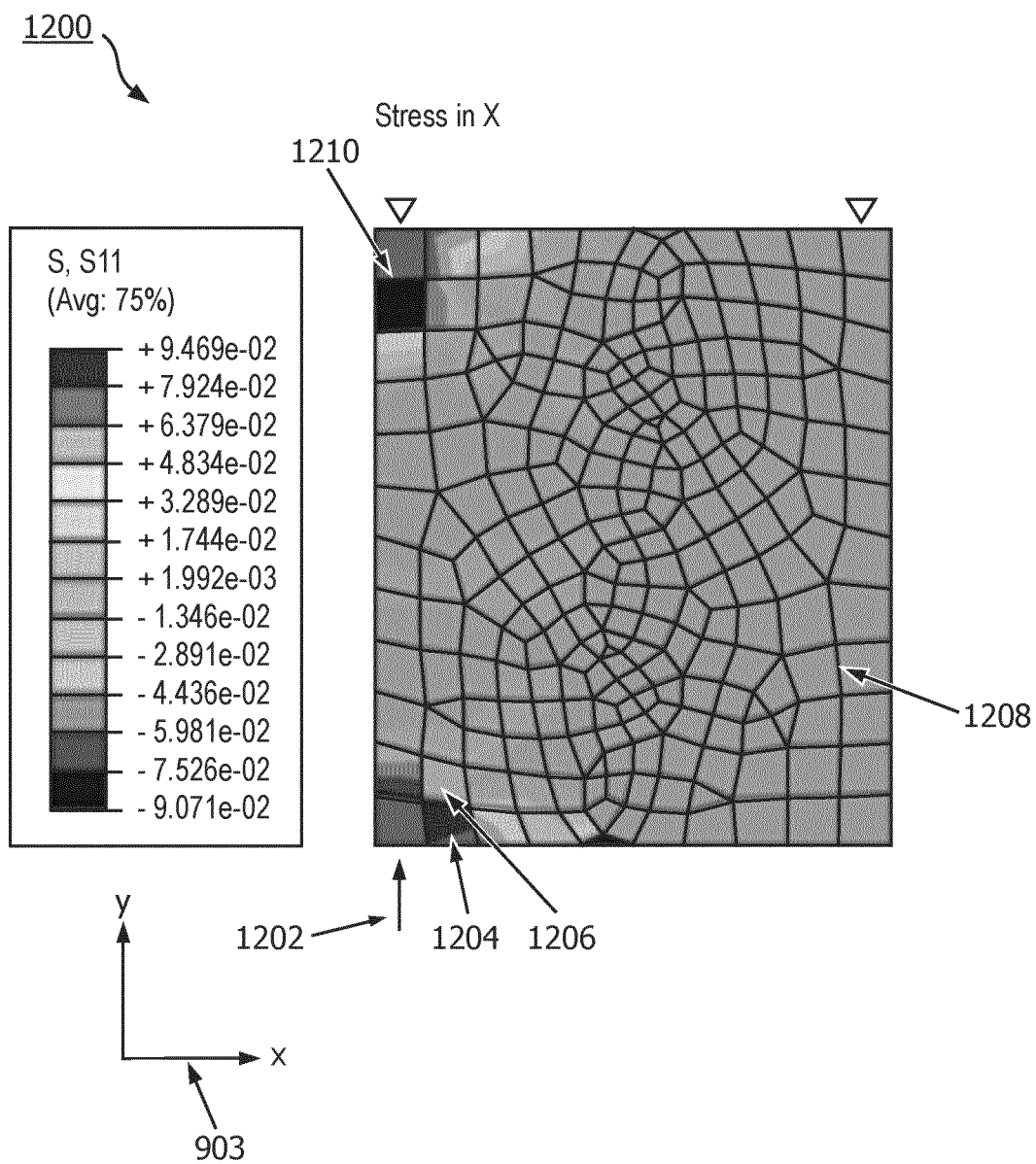
FIG. 12 is a graphical view of a finite element analysis model that demonstrates stress in x-direction under shear loading conditions of an ultrasound probe housing with sinusoidal interface according to embodiments of the present disclosure.

Similarly, FIG. 12 shows a finite element analysis model 1200 that demonstrates stress distribution points (e.g., 1204, 1206, 1208, 1210) in x-direction 903 under shear loading 1202 conditions of the ultrasound probe housing with sinusoidal interface according to embodiments of the present disclosure.

Figure 13:
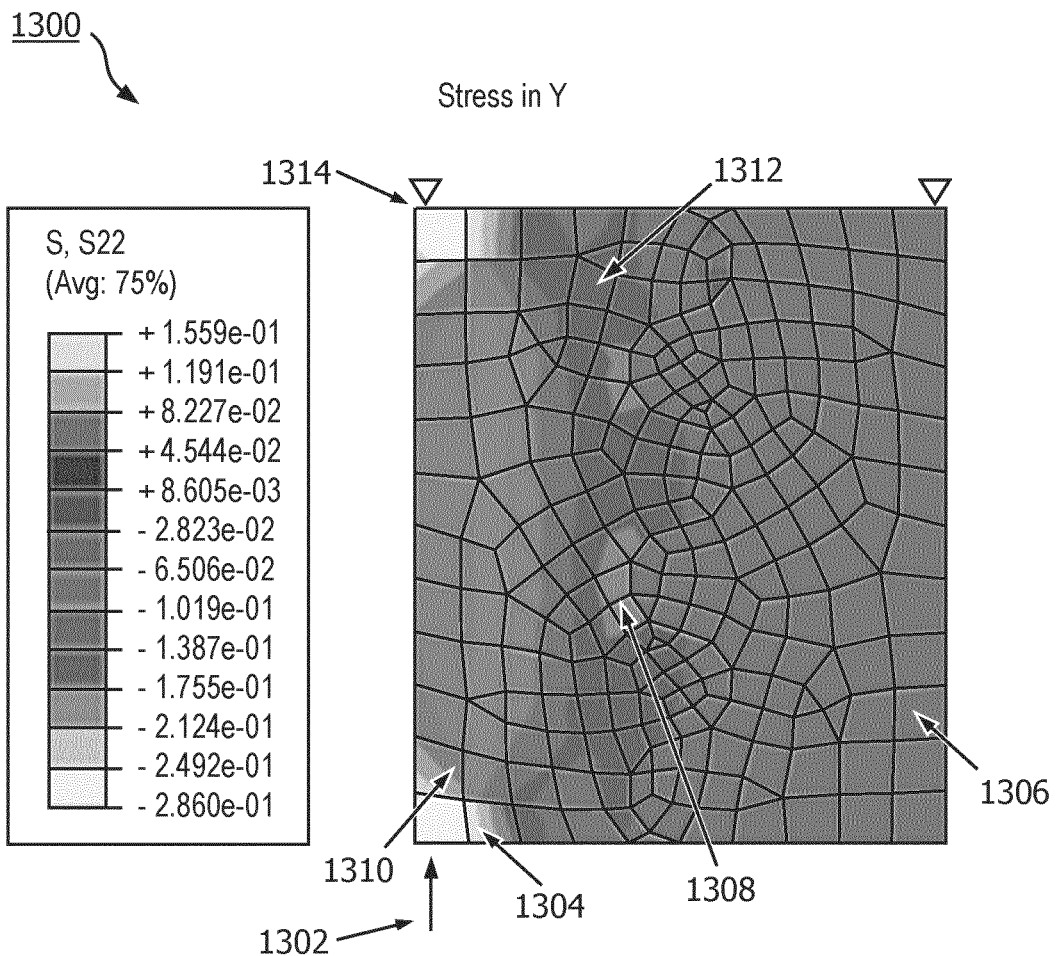
FIG. 13 is a graphical view of a finite element analysis model that demonstrates stress of an ultrasound probe housing in y-direction under shear loading conditions, according to embodiments of the present disclosure.
Figure 14:
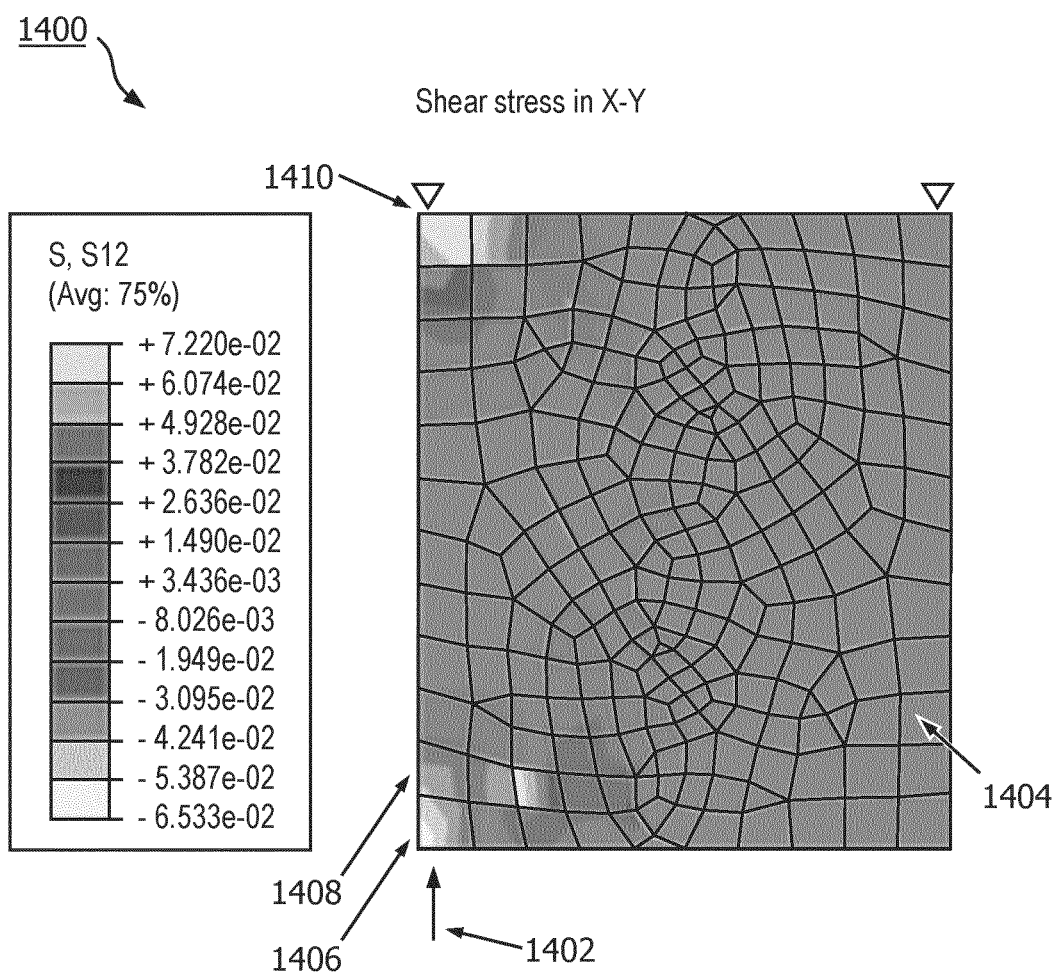
FIG. 14 is a graphical view of a finite element analysis model that demonstrates shear stress of an ultrasound probe housing in x-y-direction under shear loading conditions, according to embodiments of the present disclosure.

FIG. 13 illustrates finite element analysis model 1300 that demonstrates stress distribution points (e.g., 1304, 1306, 1308, 1310, 1312, 1314) similar to model 1200 as illustrated in FIG. 12, in y-direction 905 also under shear loading 1302 conditions of the ultrasound probe housing with the sinusoidal interface according to embodiments of the present disclosure. In illustrated embodiment of FIG. 14 finite element analysis model 1400 that demonstrates shear stress distribution points (e.g., 1404, 1406, 1408, 1410) in x-y-direction 903, 905 also under shear loading 1402 conditions of the ultrasound probe housing with the sinusoidal interface according to embodiments of the present disclosure. In the illustrated embodiments of FIGS. 12-14, the exemplary design with the sinusoidal interface under shear loading conditions resulted in offsetting tensile and compressive stresses to be generated in the normal stress directions along x-axis (FIG. 12) and y-axis (FIG. 13) while the shear stress in the x-y direction (FIG. 14) was uniformly transferred across the interface.

To fabricate an ultrasound probe housing with a sinusoidal interface, several different traditional and non-traditional manufacturing techniques may be used based on material, features and structure of the interface, including injection molding, casting, 3D printing, laser cutting and texturing, extrusion, micro-machining, co-forming, stamping, electron beam melting and/or other suitable techniques. It should be understood that no limitation to any particular manufacturing technology is intended or should be implied from the teachings of the disclosed principles.

The structure of the probe with the exemplary sinusoidal interface may be selected based on the size, shape, functional objective, and/or type of ultrasound probe. Thus, any advantageous structural arrangement with appropriate length, width, and height, may be employed, which could include not only the shapes discussed herein, but also circular segments, triangular, conic, parabolic, polygonal, and/or rectilinear shapes may also be employed. The sinusoidal interface may include any number of periods and amplitudes such as one, two, five, ten or more and variety of combination of features. All exemplary variations of the interface and may be included an ultrasound probe. The sinusoidal interface advantageously incorporates variety of material properties and structures that can facilitate multitude of purposes for any assembly that has treatment devices incorporated.

Figure 15:
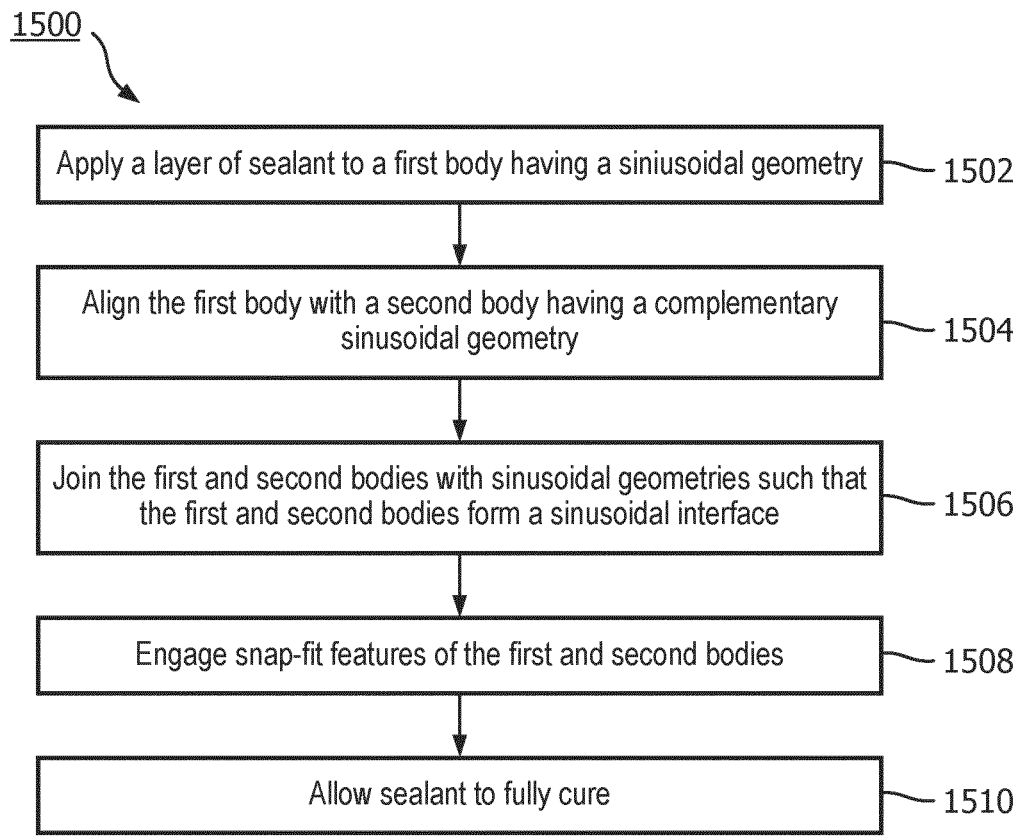
FIG. 15 is a flow diagram of a method of assembling an ultrasound probe housing with a sinusoidal snap-fit interface, according to aspects of the disclosure.

FIG. 15 illustrates a flow diagram illustrating an exemplary method 1500 of forming a medical device housing with sinusoidal snap-fit interface geometry. The steps of the method 1500 are shown with reference to steps 1502, 1504, 1506, 1508, 1510 of FIG. 15. At step 1502, the method 1500 may include application of a layer of sealant/adhesive to a first body that includes a sinusoidal geometry. The sealant serves as a barrier layer and to prevent friction that might result in wear and tear once the female and male portion are joined.

At step 1504, the method 1500 includes aligning the first body with a second body having a complementary, or opposite sinusoidal geometry configured to engage the sinusoidal geometry of the first body. In this step 1504 the increased contact area between the first and second bodies may result in a connection that is secure, facilitates uniform load transfer, and is more accommodating to shear loading conditions than conventional ultrasound probes.

At step 1506, the method 1500 includes coupling the first and second bodies with sinusoidal snap-fit geometries such that the first and second bodies form a sinusoidal interface. The formation of the sinusoidal interface between housing bodies may reduce the possibility of misalignment of the two housing bodies, which has been an issue in conventional housing designs.

At step 1508, the method 1500 may include engaging snap fit features of the first and second bodies to secure the first body to the second body. In some embodiments, steps 1506 and 1508 may be performed using a single motion. The incorporated snap-fit features may remove the need for assembly tools in production. The added mechanical retention between housing bodies may also decrease the chance of gaps forming in the housing.

At step 1510, the method 1500 may further include allow sealant to fully cure and form the final enclosure assembly of the ultrasound probe.

Figure 16:
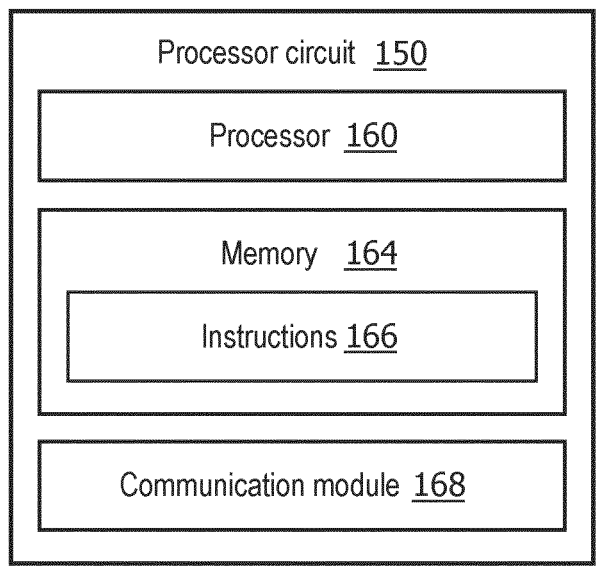
FIG. 16 is a schematic diagram of a processor circuit, according to embodiments of the present disclosure.

FIG. 16 is a schematic diagram of a processor circuit 150, according to embodiments of the present disclosure. The processor circuit 150 may be implemented in the console 102 and/or the imaging probe 108 of FIG. 1. As shown, the processor circuit 150 may include a processor 160, a memory 164, and a communication module 168. These elements may be in direct or indirect communication with each other, for example via one or more buses.

The processor 160 may include a central processing unit (CPU), a digital signal processor (DSP), an ASIC, a controller, an FPGA, another hardware device, a firmware device, or any combination thereof configured to perform the operations described herein. The processor 160 may also be implemented as a combination of computing devices, e.g., a combination of a DSP and a microprocessor, a plurality of microprocessors, one or more microprocessors in conjunction with a DSP core, or any other such configuration.

The memory 164 may include a cache memory (e.g., a cache memory of the processor 160), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 164 includes a non-transitory computer-readable medium. The memory 164 may store instructions 166. The instructions 166 may include instructions that, when executed by the processor 160, cause the processor 160 to perform the operations described herein with reference to the console 102 and/or the imaging probe 108 (FIG. 1). Instructions 166 may also be referred to as code. The terms "instructions" and "code" should be interpreted broadly to include any type of computer-readable statement(s). For example, the terms "instructions" and "code" may refer to one or more programs, routines, sub-routines, functions, procedures, etc. "Instructions" and "code" may include a single computer-readable statement or many computer-readable statements.

The communication module 168 can include any electronic circuitry and/or logic circuitry to facilitate direct or indirect communication of data between the processor circuit 150, the imaging device 102, and/or the display 108. In that regard, the communication module 168 can be an input/output (I/O) device. In some instances, the communication module 168 facilitates direct or indirect communication between various elements of the processor circuit 150 and/or the console 102 (FIG. 1).

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ultrasound probe, comprising:
a housing comprising:
a first body comprising a first proximal portion and a first distal portion, wherein the first proximal portion comprises a first sinusoidal shape; and
a second body comprising a second proximal portion and a second distal portion, wherein the second proximal portion comprises an opposite second sinusoidal shape, wherein the first body and the second body are coupled such that the first sinusoidal shape engages with the second sinusoidal shape to form a sinusoidal interface, wherein the first proximal portion and the second proximal portion form a handle configured to be grasped by a user, and wherein the first distal portion and the second distal portion form a head portion; and
an ultrasound transducer assembly configured to obtain ultrasound data, wherein the ultrasound transducer assembly is disposed at the head portion of the housing,
wherein the first body further comprises a first outer wall portion, wherein the second body comprises a second outer wall portion, wherein the first outer wall portion and the second outer wall portion extend alongside and external to the first sinusoidal shape and the second sinusoidal shape, respectively, and wherein the first outer wall portion and the second outer wall portion engage to form a straight interface when the first body is coupled to the second body.

2. The ultrasound probe of claim 1, wherein the first body and the second body comprise a polymeric material.

3. The ultrasound probe of claim 1, wherein the first outer wall portion and the second outer wall portion are shaped and arranged relative to the first sinusoidal shape and the second sinusoidal shape such that the first outer wall portion contacts the second outer wall portion when the first sinusoidal shape engages the second sinusoidal shape.

4. The ultrasound probe of claim 1, wherein the first body comprises a protrusion disposed at the sinusoidal interface, wherein the second body comprises a groove disposed at the sinusoidal interface, and wherein the protrusion and the groove lock when the first sinusoidal shape engages the second sinusoidal shape.

5. The ultrasound probe of claim 4, wherein the protrusion is positioned on an inner surface of the first outer wall portion, and wherein the groove is positioned on the first sinusoidal shape.

6. The ultrasound probe of claim 1, wherein the first body comprises a plurality of protrusions disposed at the sinusoidal interface, wherein the second body comprises a plurality of grooves disposed at the sinusoidal interface, such that the first body is configured to be coupled to the second body to form the housing by a tool-less assembly process.

7. The ultrasound probe of claim 6, further comprising an adhesive applied between the first body and the second body at the sinusoidal interface.

8. The ultrasound probe of claim 1, wherein the first sinusoidal shape comprises a plurality of projections and a plurality of recesses, wherein the first outer wall portion comprises a rim, wherein the plurality of projections is positioned above the rim, and wherein the plurality of recesses is positioned at least partially below the rim.

9. The ultrasound probe of claim 1, further comprising a cable coupled to the housing, wherein the cable comprises a plurality of conductors electrically coupled to the ultrasound transducer assembly, wherein the housing comprises a first opening at a distal end of the housing and a second opening at a proximal end of the housing, wherein the ultrasound transducer assembly is positioned within the first opening, and wherein the cable is positioned within the second opening.

10. The ultrasound probe of claim 9, wherein the sinusoidal interface extends between the first opening and the second opening.

11. The ultrasound probe of claim 1, wherein the first sinusoidal shape extends continuously along the first proximal portion and the first distal portion of the first body, and wherein the second sinusoidal shape extends continuously along the second proximal portion and the second distal portion of the second body.

12. The ultrasound probe of claim 1, wherein the sinusoidal interface comprises at least three periods.

13. The ultrasound probe of claim 1, wherein the first sinusoidal shape is offset from the second sinusoidal shape by half a period.

14. An ultrasound probe, comprising:
a housing comprising:
    a first body comprising a first proximal portion and a first distal portion, wherein the first proximal portion comprises a first sinusoidal shape; and
    a second body comprising a second proximal portion and a second distal portion, wherein the second proximal portion comprises an opposite second sinusoidal shape, wherein the first body and the second body are coupled such that the first sinusoidal shape engages with the second sinusoidal shape to form a sinusoidal interface, wherein the first proximal portion and the second proximal portion form a handle configured to be grasped by a user, and wherein the first distal portion and the second distal portion form a head portion; and
an ultrasound transducer assembly configured to obtain ultrasound data, wherein the ultrasound transducer assembly is disposed at the head portion of the housing, wherein the sinusoidal interface comprises a proximal segment extending along the handle, and a distal segment extending along the head portion, wherein the proximal segment and the distal segment comprise different sinusoidal geometries.

15. An ultrasound imaging system, comprising:
an ultrasound probe comprising:
a housing comprising:
    a first body comprising a first proximal portion and a first distal portion, wherein the first proximal portion comprises a first sinusoidal shape; and
    a second body comprising a second proximal portion and a second distal portion, wherein the second proximal portion comprises an opposite second sinusoidal shape, wherein the first body and the second body are coupled such that the first sinusoidal shape engages with the second sinusoidal shape to form a sinusoidal interface, wherein the first proximal portion and the second proximal portion form a handle configured to be grasped by a user, and wherein the first distal portion and the second distal portion form a head portion; and
an ultrasound transducer assembly configured to obtain ultrasound data, wherein the ultrasound transducer assembly is disposed at the head portion of the housing; and
a processor circuit in communication with the ultrasound probe, the processing circuit configured to generate an ultrasound image based on the ultrasound data and output the ultrasound image to a display in communication with the processor circuit,
wherein the first body further comprises a first outer wall portion, wherein the second body comprises a second outer wall portion, wherein the first outer wall portion and the second outer wall portion extend alongside and external to the first sinusoidal shape and the second sinusoidal shape, respectively, and wherein the first outer wall portion and the second outer wall portion engage to form a straight interface when the first body is coupled to the second body.

* * * * *